(12) United States Patent
Fasano et al.

(10) Patent No.: US 7,531,512 B2
(45) Date of Patent: *May 12, 2009

(54) METHOD OF USE OF PEPTIDE ANTAGONISTS OF ZONULIN TO PREVENT OR DELAY THE ONSET OF DIABETES

(75) Inventors: Alessio Fasano, West Friendship, MD (US); Tammara L. Watts, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/346,395

(22) Filed: Feb. 3, 2006

(65) Prior Publication Data

US 2006/0128626 A1 Jun. 15, 2006

Related U.S. Application Data

(63) Continuation of application No. 10/275,877, filed as application No. PCT/US01/05825 on Mar. 21, 2001, now Pat. No. 7,026,294.

(60) Provisional application No. 60/205,305, filed on May 19, 2000.

(51) Int. Cl.
*A61K 38/00* (2006.01)
*A61K 38/16* (2006.01)
*C07K 14/00* (2006.01)

(52) U.S. Cl. .............................. 514/12; 514/13; 514/14; 514/15; 514/16; 514/866; 530/324; 530/326; 530/327; 530/328; 530/350; 530/844

(58) Field of Classification Search .................. 514/12, 514/13, 14, 15, 16, 866; 530/324, 326, 327, 530/328, 350, 844
See application file for complete search history.

(56) References Cited

U.S. PATENT DOCUMENTS

| 5,665,389 | A | 9/1997 | Fasano |
| 5,945,510 | A | 8/1999 | Fasano |
| 6,458,925 | B1 | 10/2002 | Fasano |
| 6,670,448 | B2 | 12/2003 | Fasano |
| 6,936,689 | B2 | 8/2005 | Fasano |
| 7,026,294 | B2 * | 4/2006 | Fasano et al. .................. 514/12 |
| 7,189,696 | B2 | 3/2007 | Fasano |

FOREIGN PATENT DOCUMENTS

| WO | WO 96/37196 | 11/1996 |
| WO | WO 00/07609 | 2/2000 |

OTHER PUBLICATIONS

Dorland's Illustrated Medical Dictionary, 1974, Twenty-fifth Edition, W.B. Saunders. Philadelphia. London, Toronto, p. 453.*
Meddings et al., American Physiological Society, (1999), pp. G951-G957.
Watts et al., Gastroenterology, 118(4, Supp. 2, Part 1 of 2): 101st Annual Meeting of the American Gastroenterological Association, San Diego, Abstract No. 3113, (May 21-24, 2000).
Fasano et al., "Zonulin, a Newly Discovered Modulator of Intestinal Permeability, and its . . . ", The Lancet, Apr. 29, 2000, 355:1518-1519.
Tammara Watts et al., "Role of the Intestinal Tight Junction Modulator Zonulin in the Pathogenesis of Type I Diabetes in BB Diabetic-Prone Rats", PNAS (USA), vol. 102, No. 8, Feb. 22, 2005, pp. 2916-2921.

* cited by examiner

*Primary Examiner*—Jon P Weber
*Assistant Examiner*—Abdel A Mohamed
(74) *Attorney, Agent, or Firm*—Cooley Godward Kronish LLP (57) ABSTRACT

A method for preventing or delaying the onset of autoimmune diseases is disclosed.

12 Claims, 7 Drawing Sheets

| Sequence | | |
|---|---|---|
| Vibrio cholerae ZOT* (SEQ ID NO:33) | Phe Cys Ile | Gly Arg Leu Cys Val Gln Asp Gly Phe Val Thr |
| Human Adult Intestine (SEQ ID NO:28) | Glu Val Gln Leu Val Glu Ser | Gly Gly Xaa Leu | |
| Human Fetal Intestine - (SEQ ID NO:27) | Met Leu Gln Lys Ala Glu Ser | Gly Gly Val Leu Val Gln Pro Gly | Xaa Ser Asn Arg Leu |
| Human Adult Heart - (SEQ ID NO:25) | Glu Val Gln Leu Val Glu Ser | Gly Gly Gly Leu Val Gln Pro Gly | Gly Ser Leu Arg Leu |
| FZI/0 - (SEQ ID NO:15) | | Gly Gly Val Leu Val Gln Pro Gly | |
| FZI/1 - (SEQ ID NO:29) | | Val Gly Val Leu Gly Arg Pro Gly | |
| Human Fetal Brain - (SEQ ID NO:31) | Xaa Gly Lys Val Lys Val Gly | Val Asn Gly Phe Gly Arg Ile Gly | Arg Ile Gly Arg Leu Val Ile |
| Human Adult Brain - (SEQ ID NO:26) | Val Thr Phe Tyr Thr Asp Ala | Val Ser | |
| Human IgM Heavy Chain - (SEQ ID NO:36) | Glu Val Gln Leu Val Glu Ser | Gly Gly Gly Leu Val Gln Pro Gly | Arg Ser Leu Arg Leu |

FIG. 1

```
SEQUENCE LISTING

<160> NUMBER OF SEQ ID NOS: 33

<210> SEQ ID NO 1
<211> LENGTH: 8
<212> TYPE: PRT
<213> ORGANISM: Artificial
<220> FEATURE:
<223> OTHER INFORMATION: tight junction antagonist peptide

<400> SEQUENCE: 1

Gly Arg Val Cys Val Gln Pro Gly
1               5

<210> SEQ ID NO 2
<211> LENGTH: 8
<212> TYPE: PRT
<213> ORGANISM: Artificial
<220> FEATURE:
<223> OTHER INFORMATION: tight junction antagonist peptide

<400> SEQUENCE: 2

Gly Arg Val Cys Val Gln Asp Gly
1               5

<210> SEQ ID NO 3
<211> LENGTH: 8
<212> TYPE: PRT
<213> ORGANISM: Artificial
<220> FEATURE:
<223> OTHER INFORMATION: tight junction antagonist peptide

<400> SEQUENCE: 3

Gly Arg Val Leu Val Gln Pro Gly
1               5

<210> SEQ ID NO 4
<211> LENGTH: 8
<212> TYPE: PRT
<213> ORGANISM: Artificial
<220> FEATURE:
<223> OTHER INFORMATION: tight junction antagonist peptide
```

-continued

```
<400> SEQUENCE: 4

Gly Arg Val Leu Val Gln Asp Gly
1               5

<210> SEQ ID NO 5
<211> LENGTH: 8
<212> TYPE: PRT
<213> ORGANISM: Artificial
<220> FEATURE:
<223> OTHER INFORMATION: tight junction antagonist peptide

<400> SEQUENCE: 5

Gly Arg Leu Cys Val Gln Pro Gly
1               5

<210> SEQ ID NO 6
<211> LENGTH: 8
<212> TYPE: PRT
<213> ORGANISM: Artificial
<220> FEATURE:
<223> OTHER INFORMATION: tight junction antagonist peptide

<400> SEQUENCE: 6

Gly Arg Leu Cys Val Gln Asp Gly
1               5

<210> SEQ ID NO 7
<211> LENGTH: 8
<212> TYPE: PRT
<213> ORGANISM: Artificial
<220> FEATURE:
<223> OTHER INFORMATION: tight junction antagonist peptide

<400> SEQUENCE: 7

Gly Arg Leu Leu Val Gln Pro Gly
1               5

<210> SEQ ID NO 8
<211> LENGTH: 8
<212> TYPE: PRT
<213> ORGANISM: Artificial
<220> FEATURE:
<223> OTHER INFORMATION: tight junction antagonist peptide

<400> SEQUENCE: 8

Gly Arg Leu Leu Val Gln Asp Gly
1               5

<210> SEQ ID NO 9
<211> LENGTH: 8
<212> TYPE: PRT
<213> ORGANISM: Artificial
<220> FEATURE:
<223> OTHER INFORMATION: tight junction antagonist peptide

<400> SEQUENCE: 9

Gly Arg Gly Cys Val Gln Pro Gly
1               5

<210> SEQ ID NO 10
<211> LENGTH: 8
<212> TYPE: PRT
<213> ORGANISM: Artificial
<220> FEATURE:
<223> OTHER INFORMATION: tight junction antagonist peptide
```

```
<400> SEQUENCE: 10

Gly Arg Gly Cys Val Gln Asp Gly
1               5

<210> SEQ ID NO 11
<211> LENGTH: 8
<212> TYPE: PRT
<213> ORGANISM: Artificial
<220> FEATURE:
<223> OTHER INFORMATION: tight junction antagonist peptide

<400> SEQUENCE: 11

Gly Arg Gly Leu Val Gln Pro Gly
1               5

<210> SEQ ID NO 12
<211> LENGTH: 8
<212> TYPE: PRT
<213> ORGANISM: Artificial
<220> FEATURE:
<223> OTHER INFORMATION: tight junction antagonist peptide

<400> SEQUENCE: 12

Gly Arg Gly Leu Val Gln Asp Gly
1               5

<210> SEQ ID NO 13
<211> LENGTH: 8
<212> TYPE: PRT
<213> ORGANISM: Artificial
<220> FEATURE:
<223> OTHER INFORMATION: tight junction antagonist peptide

<400> SEQUENCE: 13

Gly Gly Val Cys Val Gln Pro Gly
1               5

<210> SEQ ID NO 14
<211> LENGTH: 8
<212> TYPE: PRT
<213> ORGANISM: Artificial
<220> FEATURE:
<223> OTHER INFORMATION: tight junction antagonist peptide

<400> SEQUENCE: 14

Gly Gly Val Cys Val Gln Asp Gly
1               5

<210> SEQ ID NO 15
<211> LENGTH: 8
<212> TYPE: PRT
<213> ORGANISM: Artificial
<220> FEATURE:
<223> OTHER INFORMATION: tight junction antagonist peptide

<400> SEQUENCE: 15

Gly Gly Val Leu Val Gln Pro Gly
1               5

<210> SEQ ID NO 16
<211> LENGTH: 8
<212> TYPE: PRT
<213> ORGANISM: Artificial
<220> FEATURE:
<223> OTHER INFORMATION: tight junction antagonist peptide

<400> SEQUENCE: 16
```

Gly Gly Val Leu Val Gln Asp Gly
1               5

<210> SEQ ID NO 17
<211> LENGTH: 8
<212> TYPE: PRT
<213> ORGANISM: Artificial
<220> FEATURE:
<223> OTHER INFORMATION: tight junction antagonist peptide

<400> SEQUENCE: 17

Gly Gly Leu Cys Val Gln Pro Gly
1               5

<210> SEQ ID NO 18
<211> LENGTH: 8
<212> TYPE: PRT
<213> ORGANISM: Artificial
<220> FEATURE:
<223> OTHER INFORMATION: tight junction antagonist peptide

<400> SEQUENCE: 18

Gly Gly Leu Cys Val Gln Asp Gly
1               5

<210> SEQ ID NO 19
<211> LENGTH: 8
<212> TYPE: PRT
<213> ORGANISM: Artificial
<220> FEATURE:
<223> OTHER INFORMATION: tight junction antagonist peptide

<400> SEQUENCE: 19

Gly Gly Leu Leu Val Gln Pro Gly
1               5

<210> SEQ ID NO 20
<211> LENGTH: 8
<212> TYPE: PRT
<213> ORGANISM: Artificial
<220> FEATURE:
<223> OTHER INFORMATION: tight junction antagonist peptide

<400> SEQUENCE: 20

Gly Gly Leu Leu Val Gln Asp Gly
1               5

<210> SEQ ID NO 21
<211> LENGTH: 8
<212> TYPE: PRT
<213> ORGANISM: Artificial
<220> FEATURE:
<223> OTHER INFORMATION: tight junction antagonist peptide

<400> SEQUENCE: 21

Gly Gly Gly Cys Val Gln Pro Gly
1               5

<210> SEQ ID NO 22
<211> LENGTH: 8
<212> TYPE: PRT
<213> ORGANISM: Artificial
<220> FEATURE:
<223> OTHER INFORMATION: tight junction antagonist peptide

<400> SEQUENCE: 22

```
Gly Gly Gly Cys Val Gln Asp Gly
1               5
```

<210> SEQ ID NO 23
<211> LENGTH: 8
<212> TYPE: PRT
<213> ORGANISM: Artificial
<220> FEATURE:
<223> OTHER INFORMATION: tight junction antagonist peptide

<400> SEQUENCE: 23

```
Gly Gly Gly Leu Val Gln Pro Gly
1               5
```

<210> SEQ ID NO 24
<211> LENGTH: 8
<212> TYPE: PRT
<213> ORGANISM: Artificial
<220> FEATURE:
<223> OTHER INFORMATION: tight junction antagonist peptide

<400> SEQUENCE: 24

```
Gly Gly Gly Leu Val Gln Asp Gly
1               5
```

<210> SEQ ID NO 25
<211> LENGTH: 20
<212> TYPE: PRT
<213> ORGANISM: Homo sapiens

<400> SEQUENCE: 25

```
Glu Val Gln Leu Val Glu Ser Gly Gly Gly Leu Val Gln Pro Gly Gly
1               5                   10                  15

Ser Leu Arg Leu
            20
```

<210> SEQ ID NO 26
<211> LENGTH: 9
<212> TYPE: PRT
<213> ORGANISM: Homo sapiens

<400> SEQUENCE: 26

```
Val Thr Phe Tyr Thr Asp Ala Val Ser
1               5
```

<210> SEQ ID NO 27
<211> LENGTH: 20
<212> TYPE: PRT
<213> ORGANISM: Homo sapiens
<220> FEATURE:
<221> NAME/KEY: misc_feature
<222> LOCATION: (16)..(16)
<223> OTHER INFORMATION: Xaa can be any naturally occurring amino acid

<400> SEQUENCE: 27

```
Met Leu Gln Leu Ala Glu Ser Gly Gly Val Leu Val Gln Pro Gly Xaa
1               5                   10                  15

Ser Asp Arg Leu
            20
```

<210> SEQ ID NO 28
<211> LENGTH: 11
<212> TYPE: PRT
<213> ORGANISM: Homo sapiens
<220> FEATURE:
<221> NAME/KEY: misc_feature

```
<222> LOCATION: (10)..(10)
<223> OTHER INFORMATION: Xaa can be any naturally occurring amino acid

<400> SEQUENCE: 28

Glu Val Gln Leu Val Glu Ser Gly Gly Xaa Leu
1               5                   10

<210> SEQ ID NO 29
<211> LENGTH: 8
<212> TYPE: PRT
<213> ORGANISM: Artificial
<220> FEATURE:
<223> OTHER INFORMATION: tight junction antagonist peptide

<400> SEQUENCE: 29

Val Gly Val Leu Gly Arg Pro Gly
1               5

<210> SEQ ID NO 30
<211> LENGTH: 8
<212> TYPE: PRT
<213> ORGANISM: Artificial
<220> FEATURE:
<223> OTHER INFORMATION: tight junction antagonist peptide

<400> SEQUENCE: 30

Val Asp Gly Phe Gly Arg Ile Gly
1               5

<210> SEQ ID NO 31
<211> LENGTH: 22
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 31

Xaa Gly Leu Val Leu Val Gly Val Asn Gly Phe Gly Arg Ile Gly Arg
1               5                   10                  15

Ile Gly Arg Leu Val Ile
            20

<210> SEQ ID NO 32
<211> LENGTH: 20
<212> TYPE: PRT
<213> ORGANISM: Homo sapiens

<400> SEQUENCE: 32

Glu Val Gln Leu Val Glu Ser Gly Gly Gly Leu Val Gln Pro Gly Arg
1               5                   10                  15

Ser Leu Arg Leu
            20

<210> SEQ ID NO 33
<211> LENGTH: 14
<212> TYPE: PRT
<213> ORGANISM: Vibrio cholerae

<400> SEQUENCE: 33

Phe Cys Ile Gly Arg Leu Cys Val Gln Asp Gly Phe Val Thr
1               5                   10
```

METHOD OF USE OF PEPTIDE ANTAGONISTS OF ZONULIN TO PREVENT OR DELAY THE ONSET OF DIABETES

CROSS REFERENCE TO RELATED APPLICATION

The present application is a continuation of U.S. patent application Ser. No. 10/275,877 filed Mar. 5, 2003, now U.S. Pat. No. 7,026,294, which is the national stage of PCT/US01/05825 filed Mar. 21, 2001, which PCT/US01/05825 claims the benefit under 35 USC 119(e) of Provisional Application Ser. No. 60/205,305 filed May 19, 2000.

The development of the present invention was supported by the University of Maryland, Baltimore, Md. The invention described herein was supported by funding from the National Institutes of Health (DK 48373-05). The Government has certain rights.

FIELD OF THE INVENTION

The present invention relates to use of peptide antagonists of zonulin to prevent or delay the onset of diabetes, particularly type I diabetes. The peptide antagonists bind to the zonula occludens toxin receptor, yet do not physiologically modulate the opening of mammalian tight junctions.

BACKGROUND OF THE INVENTION

I. Function and Regulation of Intestinal Tight Junctions

The intestinal epithelium represents the largest interface (more than 2,000,000 cm$^2$) between the external environment and the internal milieu. The maintenance of intercellular tight junctions ("tj") competence prevents movements of potentially harmful environmental factors, such as bacteria, viruses, toxins, food allergens, and macromolecules across the intestinal barrier. This competence is significantly jeopardized in a variety of clinical conditions affecting the gastrointestinal tract, including food allergies, enteric infections, malabsorption syndromes, and inflammatory bowel diseases.

The tj or zonula occludens (hereinafter "ZO") are one of the hallmarks of absorptive and secretory epithelia (Madara, *J. Clin. Invest.*, 83:1089-1094 (1989); and Madara, *Textbook of Secretory Diarrhea* Eds. Lebenthal et al, Chapter 11, pages 125-138 (1990)). As a barrier between apical and basolateral compartments, they selectively regulate the passive diffusion of ions and water-soluble solutes through the paracellular pathway (Gumbiner, *Am. J. Physiol.*, 253 (*Cell Physiol.* 22): C749-C758 (1987)). This barrier maintains any gradient generated by the activity of pathways associated with the transcellular route (Diamond, *Physiologist,* 20:10-18 (1977)).

Variations in transepithelial conductance can usually be attributed to changes in the permeability of the paracellular pathway, since the resistances of enterocyte plasma membranes are relatively high (Madara (1989, 1990), supra). The ZO represents the major barrier in this paracellular pathway, and the electrical resistance of epithelial tissues seems to depend on the number of transmembrane protein strands, and their complexity in the ZO, as observed by freeze-fracture electron microscopy (Madara et al, *J. Cell Biol.*, 101:2124-2133 (1985)).

There is abundant evidence that ZO, once regarded as static structures, are in fact dynamic and readily adapt to a variety of developmental (Magnuson et al, *Dev. Biol.*, 67:214-224 (1978); Revel et al, *Cold Spring Harbor Symp. Quant. Biol.*, 40:443-455 (1976); and Schneeberger et al, *J. Cell Sci.,* 32:307-324 (1978)), physiological (Gilula et al, *Dev. Biol.*, 50:142-168 (1976); Madara et al, *J. Membr. Biol.*, 100:149-164 (1987); Mazariegos et al, *J. Cell Biol.*, 98:1865-1877 (1984); and Sardet et al, *J. Cell Biol.*, 80:96-117 (1979)), and pathological (Milks et al, *J. Cell Biol.*, 103:2729-2738 (1986); Nash et al, *Lab. Invest.*, 59:531-537 (1988); and Shasby et al, *Am. J. Physiol.,* 255(*Cell Physiol.*, 24:C781-C788 (1988)) circumstances. The regulatory mechanisms that underlie this adaptation are still not completely understood. However, it is clear that, in the presence of Ca$^{2+}$, assembly of the ZO is the result of cellular interactions that trigger a complex cascade of biochemical events that ultimately lead to the formation and modulation of an organized network of ZO elements, the composition of which has been only partially characterized (Diamond, *Physiologist,* 20:10-18 (1977)). A candidate for the transmembrane protein strands, occluden, has recently been identified (Furuse et al, *J. Membr. Biol.*, 87:141-150 (1985)).

Six proteins have been identified in a cytoplasmic submembranous plaque underlying membrane contacts, but their function remains to be established (Diamond, supra). ZO-1 and ZO-2 exist as a heterodimer (Gumbiner et al, *Proc. Natl. Acad. Sci., USA,* 88:3460-3464 (1991)) in a detergent-stable complex with an uncharacterized 130 kD protein (ZO-3). Most immunoelectron microscopic studies have localized ZO-1 to precisely beneath membrane contacts (Stevenson et al, *Molec. Cell Biochem.,* 83:129-145 (1988)). Two other proteins, cingulin (Citi et al, *Nature* (London), 333:272-275 (1988)) and the 7H6 antigen (Zhong et al, *J. Cell Biol.,* 120: 477-483 (1993)) are localized further from the membrane and have not yet been cloned. Rab 13, a small GTP binding protein has also recently been localized to the junction region (Zahraoui et al, *J. Cell Biol.,* 124:101-115 (1994)). Other small GTP-binding proteins are known to regulate the cortical cytoskeleton, i.e., rho regulates actin-membrane attachment in focal contacts (Ridley et al, *Cell,* 70:389-399 (1992)), and rac regulates growth factor-induced membrane ruffling (Ridley et al, *Cell,* 70:401-410 (1992)). Based on the analogy with the known functions of plaque proteins in the better characterized cell junctions, focal contacts (Guan et al, *Nature,* 358:690-692 (1992)), and adherens junctions (Tsukita et al, *J. Cell Biol.,* 123:1049-1053 (1993)), it has been hypothesize that tj-associated plaque proteins are involved in transducing signals in both directions across the cell membrane, and in regulating links to the cortical actin cytoskeleton.

To meet the many diverse physiological and pathological challenges to which epithelia are subjected, the ZO must be capable of rapid and coordinated responses that require the presence of a complex regulatory system. The precise characterization of the mechanisms involved in the assembly and regulation of the ZO is an area of current active investigation.

There is now a body of evidence that tj structural and functional linkages exist between the actin cytoskeleton and the tj complex of absorptive cells (Gumbiner et al, supra; Madara et al, supra; and Drenchahn et al, *J. Cell Biol.,* 107: 1037-1048 (1988)). The actin cytoskeleton is composed of a complicated meshwork of microfilaments whose precise geometry is regulated by a large cadre of actin-binding proteins. An example of how the state of phosphorylation of an actin-binding protein might regulate cytoskeletal linking to the cell plasma membrane is the myristoylated alanine-rich C kinase substrate (hereinafter "MARCKS"). MARCKS is a specific protein kinase C (hereinafter "PKC") substrate that is associated with the cytoplasmic face of the plasma membrane (Aderem, *Elsevier Sci. Pub.* (UK), pages 438-443 (1992)). In its non-phosphorylated form, MARCKS crosslinks to the membrane actin. Thus, it is likely that the actin meshwork associated with the membrane via MARCKS is relatively rigid (Hartwig et al, *Nature,* 356:618-622 (1992)). Activated PKC phosphorylates MARCKS, which is released from the membrane (Rosen et al, *J. Exp. Med.,* 172:1211-1215 (1990); and Thelen et al, *Nature,* 351:320-322 (1991)). The actin linked to MARCKS is likely to be spatially separated from the membrane and be more plastic. When MARCKS is dephosphorylated, it returns to the membrane where it once again crosslinks actin (Hartwig et al, supra; and Thelen et al, supra). These data suggest that the F-actin network may be rearranged by a PKC-dependent phosphorylation process that involves actin-binding proteins (MARCKS being one of them).

A variety of intracellular mediators have been shown to alter tj function and/or structure. Tight junctions of amphibian gallbladder (Duffey et al, *Nature,* 204:451-452 (1981)), and both goldfish (Bakker et al, *Am. J. Physiol.,* 246:G213-G217 (1984)) and flounder (Krasney et al, *Fed. Proc.,* 42:1100 (1983)) intestine, display enhanced resistance to passive ion flow as intracellular cAMP is elevated. Also, exposure of amphibian gallbladder to $Ca^{2+}$ ionophore appears to enhance tj resistance, and induce alterations in tj structure (Palant et al, *Am. J. Physiol.,* 245:C203-C212 (1983)). Further, activation of PKC by phorbol esters increases paracellular permeability both in kidney (Ellis et al, C. *Am. J. Physiol.,* 263 (*Renal Fluid Electrolyte Physiol.* 32):F293-F300 (1992)), and intestinal (Stenson et al, C. *Am. J. Physiol.,* 265(*Gastrointest. Liver Physiol.,* 28):G955-G962 (1993)) epithelial cell lines.

II. Zonula Occludens Toxin

Most *Vibrio cholerae* vaccine candidates constructed by deleting the ctxA gene encoding cholera toxin (CT) are able to elicit high antibody responses, but more than one-half of the vaccinees still develop mild diarrhea (Levine et al, *Infect. Immun.,* 56(1):161-167 (1988)). Given the magnitude of the diarrhea induced in the absence of CT, it was hypothesized that *V. cholerae* produce other enterotoxigenic factors, which are still present in strains deleted of the ctxA sequence (Levine et al, supra). As a result, a second toxin, zonula occludens toxin (hereinafter "ZOT") elaborated by *V. cholerae* and which contribute to the residual diarrhea, was discovered (Fasano et al, *Proc. Natl. Acad. Sci., USA,* 8:5242-5246 (1991)). The zot gene is located immediately adjacent to the ctx genes. The high percent concurrence of the zot gene with the ctx genes among *V. cholerae* strains (Johnson et al, *J. Clin. Microb.,* 31/3:732-733 (1993); and Karasawa et al, *FEBS Microbiology Letters,* 106:143-146 (1993)) suggests a possible synergistic role of ZOT in the causation of acute dehydrating diarrhea typical of cholera. Recently, the zot gene has also been identified in other enteric pathogens (Tschape, *2nd Asian-Pacific Symposium on Typhoid fever and other Salomellosis,* 47(Abstr.) (1994)).

It has been previously found that, when tested on rabbit *ileal mucosa,* ZOT increases the intestinal permeability by modulating the structure of intercellular tj (Fasano et al, supra). It has been found that as a consequence of modification of the paracellular pathway, the intestinal mucosa becomes more permeable. It also was found that ZOT does not affect $Na^+$-glucose coupled active transport, is not cytotoxic, and fails to completely abolish the transepithelial resistance (Fasano et al, supra)

More recently, it has been found that ZOT is capable of reversibly opening tj in the intestinal mucosa, and thus ZOT, when co-administered with a therapeutic agent, e.g., insulin, is able to effect intestinal delivery of the therapeutic agent, when employed in an oral dosage composition for intestinal drug delivery, e.g., in the treatment of diabetes (WO 96/37196; U.S. Pat. No. 5,827,534; U.S. Pat. No. 5,665,389; and Fasano et al, *J. Clin. Invest.,* 99:1158-1164 (1997); each of which is incorporated by reference herein in their entirety). It has also been found that ZOT is capable of reversibly opening tj in the nasal mucosa, and thus ZOT, when co-administered with a therapeutic agent, is able to enhance nasal absorption of a therapeutic agent (U.S. Pat. No. 5,908, 825; which is incorporated by reference herein in its entirety).

In U.S. Pat. No. 5,864,014; which is incorporated by reference herein in its entirety, a ZOT receptor has been identified and purified from an intestinal cell line, i.e., CaCo2 cells. Further, in U.S. Pat. No. 5,912,323; which is incorporated by reference herein in its entirety, ZOT receptors from human intestinal, heart and brain tissue have been identified and purified. The ZOT receptors represent the first step of the paracellular pathway involved in the regulation of intestinal and nasal permeability.

III. Zonulin

In U.S. Pat. Nos. 5,945,510 and 5,948,629, which are incorporated by reference herein in their entirety, mammalian proteins that are immunologically and functionally related to ZOT, and that function as the physiological modulator of mammalian tight junctions, have been identified and purified. These mammalian proteins, referred to as "zonulin", are useful for enhancing absorption of therapeutic agents across tj of intestinal and nasal mucosa, as well as across tj of the blood brain barrier.

IV. Peptide Antagonists of Zonulin

Peptide antagonists of zonulin were identified and described for the first time in pending U.S. patent application Ser. No. 09/127,815, filed Aug. 3, 1998, which is incorporated by reference herein in its entirety, which corresponds to WO 00/07609. Said peptide antagonists bind to the ZOT receptor, yet do not function to physiologically modulate the opening of mammalian tight junctions. The peptide antagonists competitively inhibit the binding of ZOT and zonulin to the ZOT receptor, thereby inhibiting the ability of ZOT and zonulin to physiologically modulate the opening of mammalian tight junctions.

V. Diabetes

The morbidity and mortality associated with diabetes is devastating. The total number of diabetic individuals in the United States is 15.7 million. Of these, 100% of the type I diabetic individuals and 40% of type II diabetic individuals depend on parenteral administration of insulin. On an annual basis, the direct medical costs associated with diabetes exceeds 40 billion dollars. An additional 14 billion dollars is associated with disability, work loss, and premature mortality.

Although oral insulin drug delivery strategies have been the focus of many research efforts, they have been largely unsuccessful because the physiologic nature of the small intestine prevents the absorption of macromolecules, such as insulin.

An oral dosage composition comprising ZOT for targeting delivery of insulin to the paracellular pathway for the treatment of diabetes has been described in U.S. Pat. Nos. 5,827, 534 and 5,665,389. By physiologically modulating the paracellular pathway using ZOT, it is now possible to introduce a wide variety of therapeutic agents into the systemic circulation. This drug delivery system adds targeting specificity, which has long hampered the design of many oral pharmaceutical agents. The utility of this system is not limited to insulin delivery, and may represent a new way of designing orally administered pharmaceutical agents.

While offering an innovative treatment strategy for a disease as debilitating as diabetes is promising, preventing or delaying the onset of disease has widespread implications. Understanding the pathogenesis of any disease process is a daunting task. Heretofore, there has been no prior evidence of a pharmaceutical agent with the capability of preventing or delaying the onset of diabetes. In the present invention new light has been shed on the pathogenesis, prevention and delaying of onset of diabetes by demonstrating that a critical and early step in disease progression resides in alterations in paracellular permeability. In the present invention, it has been demonstrated that an increase in paracellular permeability is necessary for the progression toward diabetes. Peptide antagonists of zonulin, which block this endogenous pathway, have been found in the present invention to prevent the progression to diabetes. Thus, the present invention is believed to be useful to prevent long-term complications of diabetes. Further, the permeability changes associated with autoimmune diseases are long standing, and early intervention per the present invention is believed to have untold benefits to the diabetic patient.

SUMMARY OF THE INVENTION

An object of the present invention is to provide a method for the prevention or delay the onset of diabetes.

This and other objects of the present invention, which will be apparent from the detailed description of the invention provided hereinafter, have been met, in one embodiment, by a method for preventing or delay the onset of diabetes (particularly, type I diabetes) comprising administering to a subject in need of such prevention or delay of onset, a pharmaceutically effective amount of a peptide antagonist of zonulin, wherein said peptide antagonist binds to ZOT receptor, yet does not physiologically modulate the opening of mammalian tight junctions.

DETAILED DESCRIPTION OF THE INVENTION

As discussed above, in one embodiment, the above-described object of the present invention have been met by a method for preventing or delaying the onset of diabetes (particularly, type I diabetes) comprising administering to a subject in need of such prevention or delay of onset, a pharmaceutically effective amount of a peptide antagonist of zonulin, wherein said peptide antagonist binds to ZOT receptor, yet does not physiologically modulate the opening of mammalian tight junctions The particular peptide antagonist of zonulin employed in the present invention is not critical thereto. Examples of said peptide antagonists include peptides which comprise an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID. NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24.

The size of the peptide antagonist is not critical to the present invention. Generally, the size of the peptide antagonist will range from 8 to 110, amino acids, preferably from 8 to 40 amino acids, more preferably will be 8 amino acids.

The peptide antagonists can be chemically synthesized and purified using well-known techniques, such as described in *High Performance Liquid Chromatography of Peptides and Proteins: Separation Analysis and Conformation*, Eds. Mant et al, C.R.C. Press (1991), and a peptide synthesizer, such as Symphony (Protein Technologies, Inc); or by using recombinant DNA techniques, i.e., where the nucleotide sequence encoding the peptide is inserted in an appropriate expression vector, e.g., an *E. coli* or yeast expression vector, expressed in the respective host cell, and purified therefrom using well-known techniques.

The peptide antagonists can be administered as oral dosage compositions for small intestinal delivery. Such oral dosage compositions for small intestinal delivery are well-known in the art, and generally comprise gastroresistent tablets or capsules (*Remington's Pharmaceutical Sciences*, 16th Ed., Eds. Osol, Mack Publishing Co., Chapter 89 (1980); Digenis et al, *J. Pharm. Sci.*, 83:915-921 (1994); Vantini et al, *Clinica Terapeutica*, 145:445-451 (1993); Yoshitomi et al, *Chem. Pharm. Bull.*, 40:1902-1905 (1992); Thoma et al, *Pharmazie*, 46:331-336 (1991); Morishita et al, *Drug Design and Delivery*, 7:309-319 (1991); and Lin et al, *Pharmaceutical Res.*, 8:919-924 (1991)); each of which is incorporated by reference herein in its entirety).

Tablets are made gastroresistent by the addition of, e.g., either cellulose acetate phthalate or cellulose acetate terephthalate.

Capsules are solid dosage forms in which the peptide antagonist(s) is enclosed in either a hard or soft, soluble container or shell of gelatin. The gelatin used in the manufacture of capsules is obtained from collagenous material by hydrolysis. There are two types of gelatin. Type A, derived from pork skins by acid processing, and Type B, obtained from bones and animal skins by alkaline processing. The use of hard gelatin capsules permit a choice in prescribing a single peptide antagonist or a combination thereof at the exact dosage level considered best for the individual subject. The hard gelatin capsule consists of two sections, one slipping over the other, thus completely surrounding the peptide antagonist. These capsules are filled by introducing the peptide antagonist, or gastroresistent beads containing the peptide antagonist, into the longer end of the capsule, and then slipping on the cap. Hard gelatin capsules are made largely from gelatin, FD&C colorants, and sometimes an opacifying agent, such as titanium dioxide. The USP permits the gelatin for this purpose to contain 0.15% (w/v) sulfur dioxide to prevent decomposition during manufacture.

In the context of the present invention, oral dosage compositions for small intestinal delivery also include liquid compositions which contain aqueous buffering agents that prevent the peptide antagonist from being significantly inactivated by gastric fluids in the stomach, thereby allowing the peptide antagonist to reach the small intestines in an active form. Examples of such aqueous buffering agents which can be employed in the present invention include bicarbonate buffer (pH 5.5 to 8.7, preferably about pH 7.4).

When the oral dosage composition is a liquid composition, it is preferable that the composition be prepared just prior to administration so as to minimize stability problems. In this case, the liquid composition can be prepared by dissolving lyophilized peptide antagonist in the aqueous buffering agent.

The pharmaceutically effective amount of peptide antagonist employed is not critical to the present invention and will vary depending upon the age, weight and sex of the subject being treated. Generally, the amount of peptide antagonist employed in the present invention to prevent or delay the onset of diabetes, is in the range of about $7.5\times10^{-6}$ M to $7.5\times10^{-3}$ M, preferably about $7.5\times10^{-6}$ M to $7.5\times10^{-4}$ M. To achieve such a final concentration in, e.g., the intestines or blood, the amount of peptide antagonist in a single oral dosage composition of the present invention will generally be about 1.0 μg to 1000 μg, preferably about 1.0 μg to 100 μg.

The following examples are provided for illustrative purposes only, and are in no way intended to limit the scope of the present invention.

EXAMPLE 1

Peptide Antagonists of Zonulin

Figure 1:
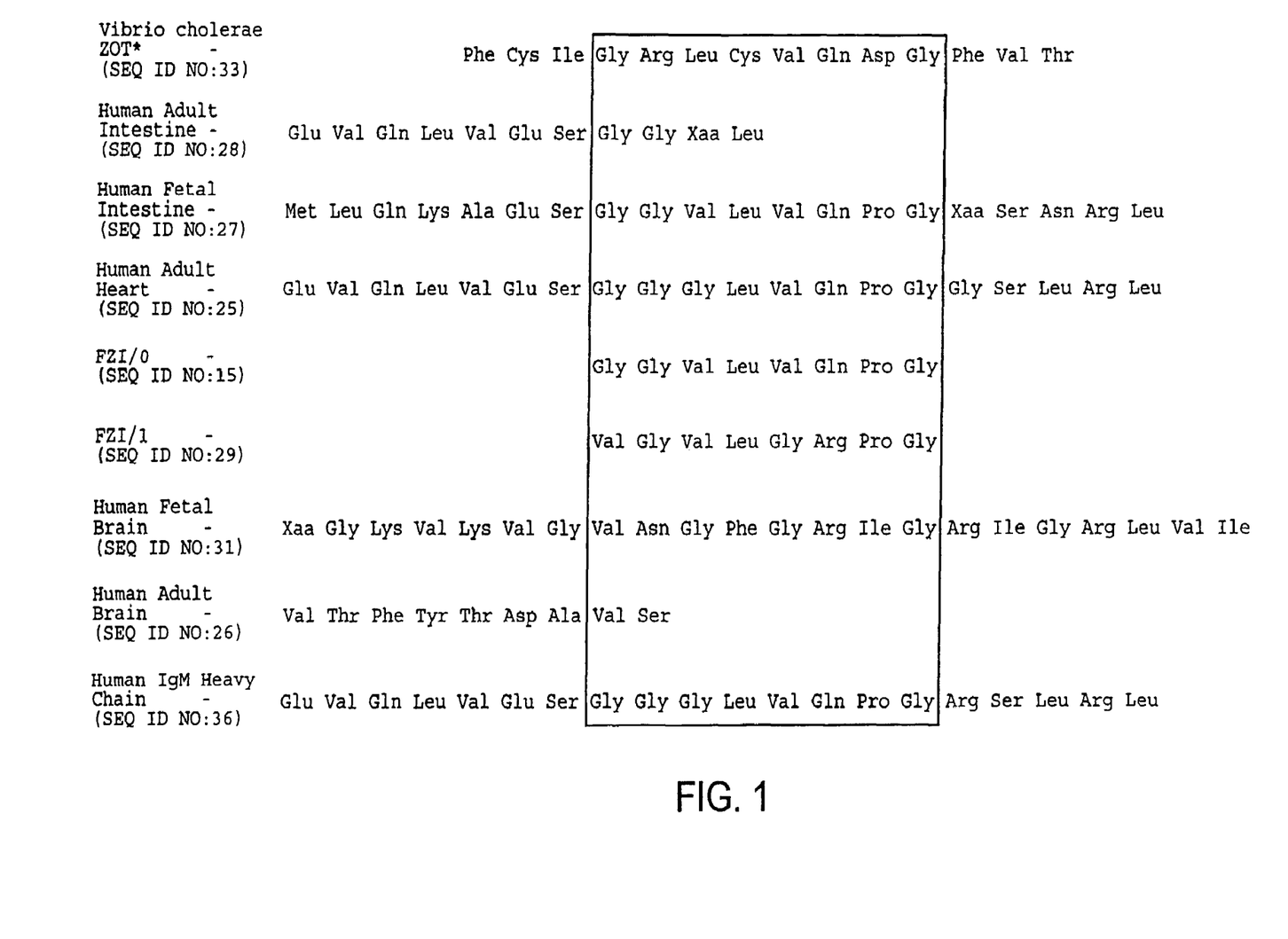
FIG. 1 shows a comparison of the N-terminal sequences of zonulin purified from various human tissues and IgM heavy chain with the N-terminal sequence of the biologically active fragment (amino acids 288-399) of ZOT.

Given that ZOT, human intestinal zonulin (zonulin$_i$) and human heart zonulin (zonulin$_h$) all act on intestinal (Fasano et al, *Gastroenterology*, 112:839 (1997); Fasano et al, *J. Clin. Invest.*, 96:710 (1995)) and endothelial tj and that all three have a similar regional effect (Fasano et al (1997), supra) that coincides with the ZOT receptor distribution within the intestine (Fasano et al (1997), supra; and Fasano et al (1995), supra), it was postulated in U.S. patent application Ser. No. 09/127,815, filed Aug. 3, 1998, that these three molecules interact with the same receptor binding site. A comparison of the primary amino acid structure of ZOT and the human zonulins was thus carried out therein to provide insights as to the absolute structural requirements of the receptor-ligand interaction involved in the regulation of intestinal tj. The analysis of the N-termini of these molecules revealed the following common motif (amino acid residues 8-15 boxed in FIG. 1): non-polar (Gly for intestine, Val for brain), variable, non-polar, variable, non-polar, polar, variable, polar (Gly). Gly in position 8, Val in position 12 and Gln in position 13, all are highly conserved in ZOT, zonulin$_i$ and zonulin$_h$ (see FIG. 1), which is believed to be critical for receptor binding function within the intestine. To verify the same, the synthetic octapeptide Gly Gly Val Leu Val Gln Pro Gly (SEQ ID NO:15) (named FZI/0, and corresponding to amino acid residues 8-15 of human fetal zonulin$_i$) was chemically synthesized.

Next, rabbit ileum mounted in Ussing chambers as described above, were exposed to 100 μg of FZI/0 (SEQ ID NO:15), 100 μg of FZI/1 (SEQ ID NO:29), 1.0 μg of 6×His-ZOT (obtained as described in Example 1 of U.S. patent application Ser. No. 09/127,815, filed Aug. 3, 1998), 1.0 μg of zonulin$_i$ (obtained as described in Example 3 of U.S. patent application Ser. No. 09/127,815, filed Aug. 3, 1998), or 1.0 μg of zonulin$_h$ (obtained as described in Example 3 of U.S. patent application Ser. No. 09/127,815, filed Aug. 3, 1998), alone; or pre-exposed for 20 min to 100 μg of FZI/0 or FZI/1, at which time 1.0 μg of 6×His-ZOT, 1.0 μg of zonulin$_i$, or 1.0 μg of zonulin$_h$, was added. ΔRt was then calculated as described above. The results are shown in FIG. 2.

Figure 2:
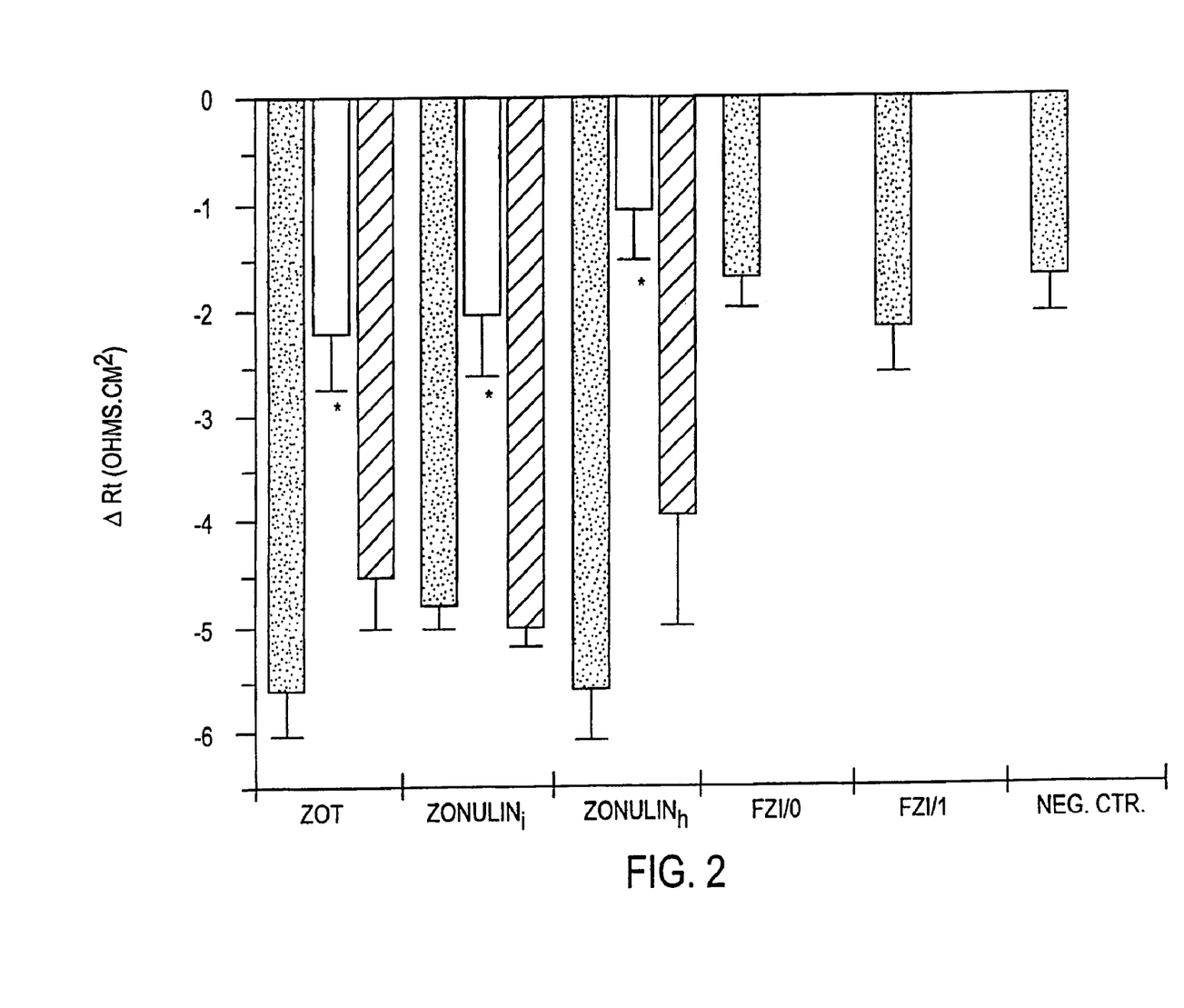
FIG. 2 shows the effect of ZOT, zonulin$_i$, zonulin$_h$, either alone (closed bars), or in combination with the peptide antagonist FZI/0 (open bars) or in combination with FZI/1 (shaded bars), as compared to the negative control, on the tissue resistance (Rt) of rabbit ileum mounted in Ussing chambers. N equals 3-5; and * equals $p<0.01$.

As shown in FIG. 2, FZI/0 did not induce any significant change in Rt (0.5% as compared to the negative control) (see closed bar). On the contrary, pre-treatment for 20 min with FZI/0 decreased the effect of ZOT, zonulin$_i$, and zonulin$_h$ on Rt by 75%, 97%, and 100%, respectively (see open bar). Also as shown in FIG. 2, this inhibitory effect was completely ablated when a second synthetic peptide (FZI/1, SEQ ID NO:29) was chemically synthesized by changing the Gly in position 8, the Val in position 12, and the Gln in position 13 (as referred to zonulin$_i$) with the correspondent amino acid residues of zonulin$_h$ (Val, Gly, and Arg, respectively, see SEQ ID NO:30) was used (see shaded bar).

The above results demonstrate that there is a region spanning between residue 8 and 15 of the N-terminal end of ZOT and the zonulin family that is crucial for the binding to the target receptor, and that the amino acid residues in position 8, 12 and 13 determine the tissue specificity of this binding.

EXAMPLE 2

Diabetic Rat Model

Alterations in intestinal permeability have been shown to be one of the preceding physiologic changes associated with the onset of diabetes (Meddings, *Am. J. Physiol.*, 276:G951-957 (1999)). Paracellular transport and intestinal permeability is regulated by intracellular tj via mechanisms which have not been completely elucidated.

Zonulin and its prokaryotic analog, ZOT, both alter intestinal permeability by modulating tj. In this example, it has been demonstrated for the first time that zonulin-related impairment of tj is involved in the pathogenesis of diabetes, and that diabetes can be prevented, or the onset delayed, by administration of a peptide antagonist of zonulin.

Initially, two genetic breeds, i.e., BB/Wor diabetic-prone (DP) and diabetic-resistant (DR) rats (Haber et al, *J. Clin. Invest.*, 95:832-837 (1993)), were evaluated to determine whether they exhibited significant changes in intraluminal secretion of zonulin and intestinal permeability.

More specifically, age-matched DP and DR rats (20, 50, 75, and >100 days of age) were sacrificed. After the rats were sacrificed, a 25G needle was placed within the lumen of the ileum, and intestinal lavage with Ringer's solution was performed to determine the presence of intraluminal zonulin. Zonulin concentration was evaluated using a sandwich enzyme linked immunosorbent assay (ELISA) as follows:

Plastic microtiter plates (Costar, Cambridge, Mass.) were coated with polyclonal rabbit anti-ZOT antibodies (obtained as described in Example 2 of U.S. application Ser. No. 09/127,815; filed Aug. 3, 1998) (dilution 1:100) overnight at 4° C., washed three times with PBS containing 0.05% (v/v) Tween 20, then blocked by incubation with 300 µl of PBS containing 0.1% (v/v) Tween 20, for 15 min at room temperature. Next, purified human intestine zonulin (obtained as described in Example 3 of U.S. application Ser. No. 09/127, 815 filed Aug. 3, 1998) was coated on the plates.

A standard curve was obtained by diluting zonulin in PBS containing 0.05% (v/v) Tween 20 at different concentration: 0.78 ng/ml, 1.56 ng/ml, 3.125 ng/ml, 6.25 ng/ml, 12.5 ng/ml, 25 ng/ml and 50 ng/ml.

100 µl of each standard concentration or 100 µl of intestinal lavage sample were pipetted into the wells, and incubated for 1 hr at room temperature, using a plate shaker. Unbound zonulin was washed-out using PBS, and the wells were incubated with 100 µl of anti-ZOT antibodies conjugated with alkaline phosphate for 1 hr at room temperature with shaking. Unbound conjugate was washed-out with PBS, and a color reaction was developed by first adding 100 µl of Extra-Avidin (SIGMA, St. Louis, Mo.) diluted 1/20000 in 0.1 M Tris-HCl (pH 7.3), 1.0 mM $MgCl_2$, 1.0% (w/v) BSA for 15 min, and then incubating each well for 30 min at 37° C. with 100 µl of a solution containing 1.0 mg/ml of p-nitrophenyl-phosphate substrate (SIGMA, St Louis, Mo.). Absorbance was read on an enzyme immunoassay reader at 405 nm.

In order to evaluate the intra- and inter-assay precision of the ELISA-sandwich method, the coefficient variation (CV) was calculated using three replicates from two samples with different concentrations of zonulin, on three consecutive days. The inter-assay test of the ELISA-sandwich method produced CV values of 9.8%. The CV of the intra-assay test was 4.2% at day 1, 3.3% at day 2 and 2.9% at day 3.

Zonulin concentration was expressed as ng/mg protein detected in the intestinal lavages and normalized by exposed surface area (in $mm^2$). The results are shown in FIG. 3.

Figure 3:
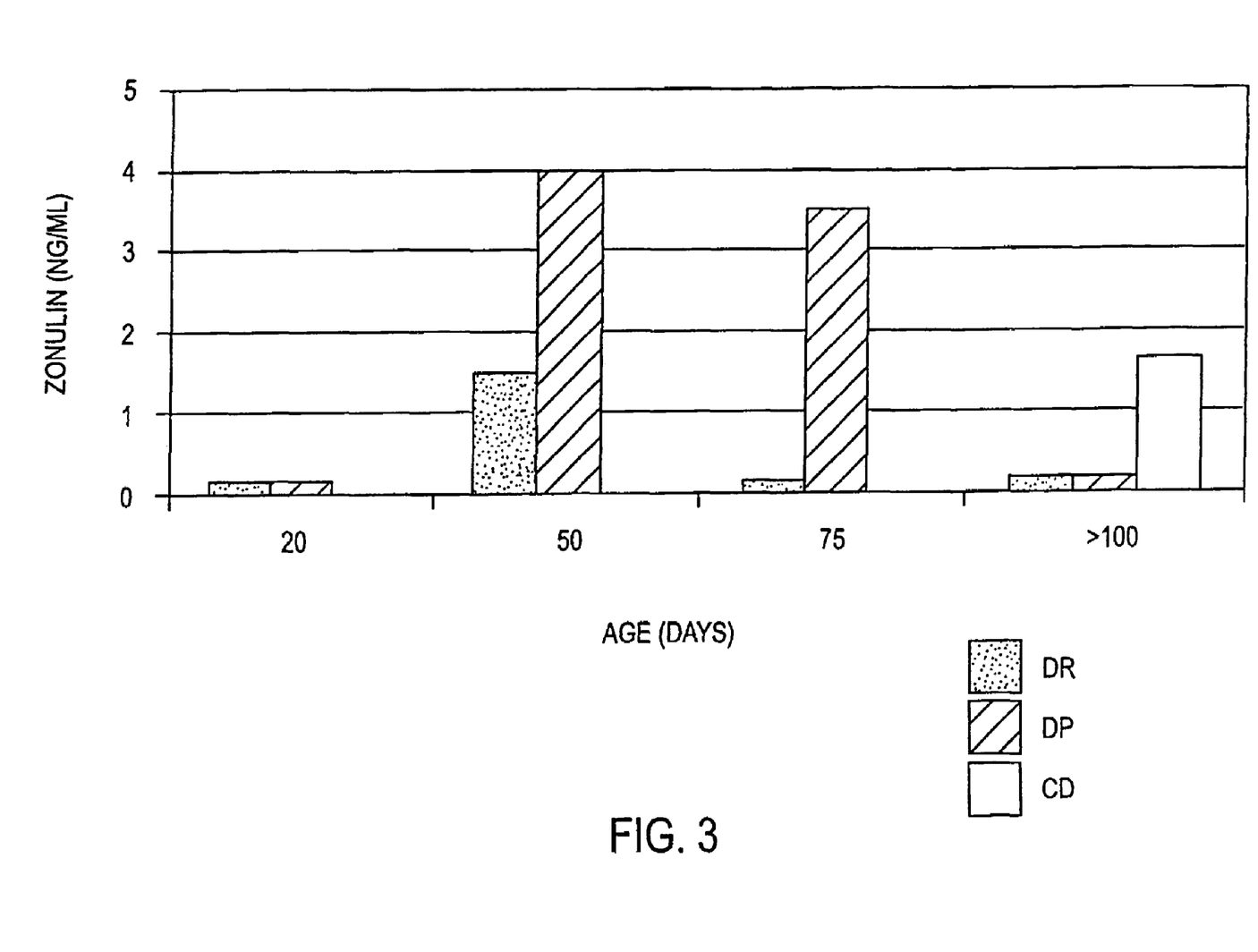
FIG. 3 shows the concentrations (ng/ml) of intraluminal zonulin in both diabetic-prone and diabetic-resistant rats, which was determined using a sandwich ELISA assay. Samples were obtained by intestinal lavage in normal saline. The first bar in each case represents diabetic-resistant rats (DR). The second bar represents diabetic-prone animals (DP), and the third bar represents rats with chronic diabetes (CD). <9% of the diabetic-prone rats do not become diabetic, and <9% of the diabetic-resistant rats develop diabetes.

As shown in FIG. 3, a 4-fold increase in intraluminal zonulin was first observed in diabetic-prone rats (age 50 days) (second bar). This increase in intraluminal zonulin was found to correlate with an increase in intestinal permeability. The increase in intraluminal zonulin remains high in these diabetic-prone rats, and found to correlate with the progression toward full-blown diabetes. Of note, the diabetic-prone rat (age >100 days) did not have an increase in intraluminal zonulin. This is remarkable, as this rat did not progress to diabetes. Blood glucose for this rat was normal. Thus, zonulin is responsible for the permeability changes associated with the pathogenesis of type I diabetes. The increase in zonulin secretion is age-related, and proceeds the onset of diabetes.

Next, in order to demonstrate that diabetes can be prevented by administration of a peptide antagonist of zonulin, BB/Wor rats (ages 21-26 days), were obtained from Biomedical Research Models, Inc. (Rutland, Mass.), and were randomized into two groups (n=5 per group), i.e., a treated group and a control group. Both groups were maintained on a standard diet of rat chow (Harlan Teklab Diet #7012). All food and water were previously autoclaved. Each day, daily water intake was measured and 100 ml of fresh water was given. The treated group received 10 µg/ml of the zonulin peptide antagonist (SEQ ID NO:15) supplemented in the drinking water. The rats were housed in hepa-filter cages.

Diabetes in the rats was diagnosed as follows: The rats were weighed twice a week. Blood glucose was determined weekly using the OneTouch® glucose monitoring system (Johnson & Johnson). Each week, reagent strips for urinalysis were used to monitor glucose (DIASTIX® glucose reagent strips) and ketones (KETOSITX® ketone test strips) (Bayer). Rats with a blood glucose >250 mg/dl were fasted overnight, and blood glucose levels >200 mg/dl were considered diabetic. These guidelines are in accordance with the data supplied by Biomedical Research Models, Inc. The results are shown in FIG. 4.

Figure 4:
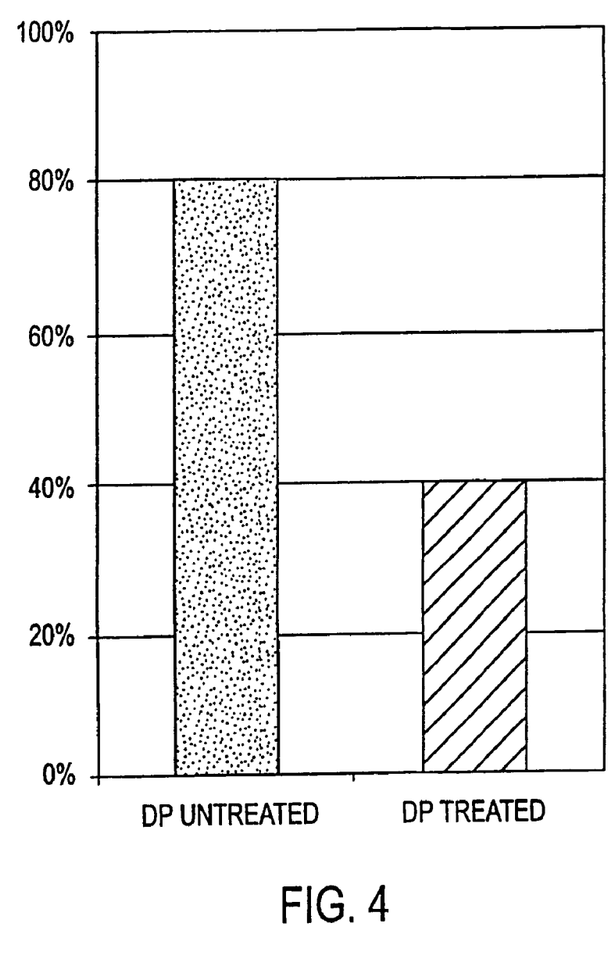
FIG. 4 shows the percentage of rats used in the study that progressed to diabetes.

As shown in FIG. 4, 80% of the control rats (4/5) and 40% of the rats treated with the peptide antagonist of zonulin (2/5) developed diabetes by age 80 days. Alterations in zonulin secretion paralleled the onset of diabetes.

Following clinical presentation of diabetes, the rats were sacrificed as follows: the rats were anesthesized using ketamine anesthesia and a midline incision was made allowing access to the heart. An 18G needle was placed into the heart and death occurred by exsanguinations. Then, zonulin assays were conducted as described above. For those rats that did not present with diabetes, the endpoint of the study was age 80 days. According to Biomedical Research Models, Inc., 80% of diabetes prone rats present with diabetes by age 80 days. The results of the zonulin assays are shown in FIG. 5.

Figure 5:
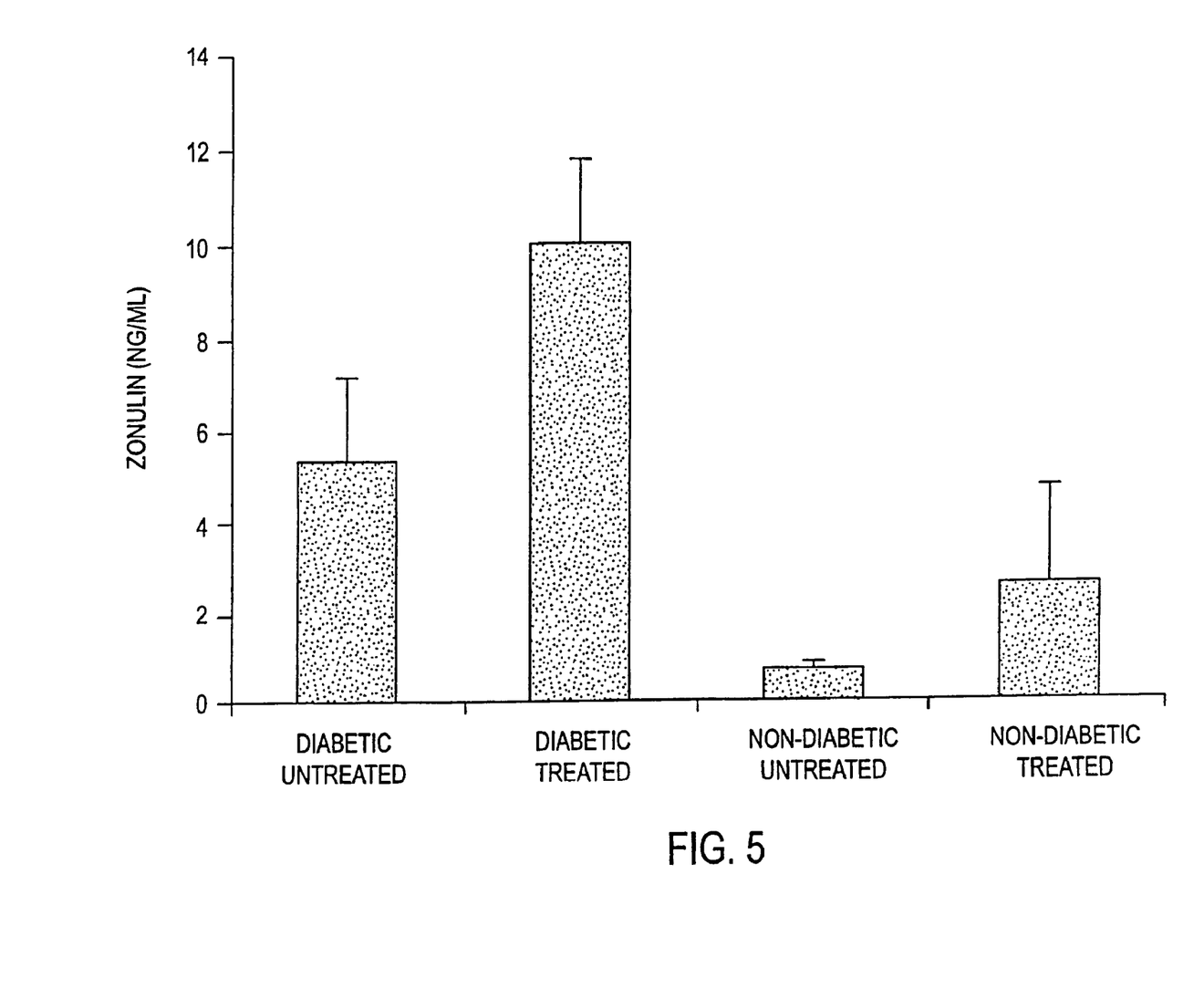
FIG. 5 shows the concentrations (ng/ml) of intraluminal zonulin in diabetic rats, which was determined using a sandwich ELISA assay.

As shown in FIG. 5, the diabetic rats that were not treated with the peptide antagonist of zonulin were observed to have an increase in intraluminal zonulin, which was consistent with the results shown in FIG. 3. Further, intraluminal zonulin was increased 2 to 4-fold in diabetic rats (DR), as compared to both diabetic-prone rats that did not develop diabetes (DP-treated) and control rats (DP-untreated). Non-diabetic control rats that did not develop diabetes had negligible levels of zonulin, consistent with the levels of zonulin shown in FIG. 3. Moreover, two diabetic-prone rats that developed diabetes despite treatment with the peptide antagonist of zonulin showed intraluminal zonulin levels that were significantly higher than the successfully treated rats, and the untreated control rats. The levels of zonulin were sufficient to initiate the permeability changes necessary to progress to diabetes, but the ZOT/zonulin receptors were effectively blocked by the peptide antagonist.

Also, following clinical presentation of diabetes, the intestinal tissues of the sacrificed rats were mounted in Ussing chamber to assess for changes in ex vivo permeability.

More specifically, sections of jejunum and ileum were isolated from the sacrificed rats, and rinsed free of intestinal contents. Six sections of each intestinal segment was prepared and mounted in Lucite Ussing chambers (0.33 $cm^2$ opening), connected to a voltage clamp apparatus (EVC 4000; World Precision Instruments, Saratosa, Fla.), and bathed with freshly prepared buffer comprising 53 mM NaCl, 5.0 mM KCl, 30.5 mM $Na_2SO_4$, 30.5 mM mannitol, 1.69 mM $Na_2PO_4$, 0.3 mM $NaHPO_4$, 1.25 mM $CaCl_2$, 1.1 mM $MgCl_2$, and 25 mN $NaHCO_3$ (pH 7.4). The bathing solution was maintained at 37° C. with water-jacketed reservoirs connected to a constant temperature circulating pump and gassed with 95% $O_2$ and 5% $CO_2$. Potential difference was measured and short-circuit current and tissue resistance was calculated as described by Fasano et al, *Proc. Natl. Acad. Sci. USA*, 88:5242-5246 (1991). The results are shown in FIGS. 6-7.

Figure 6:
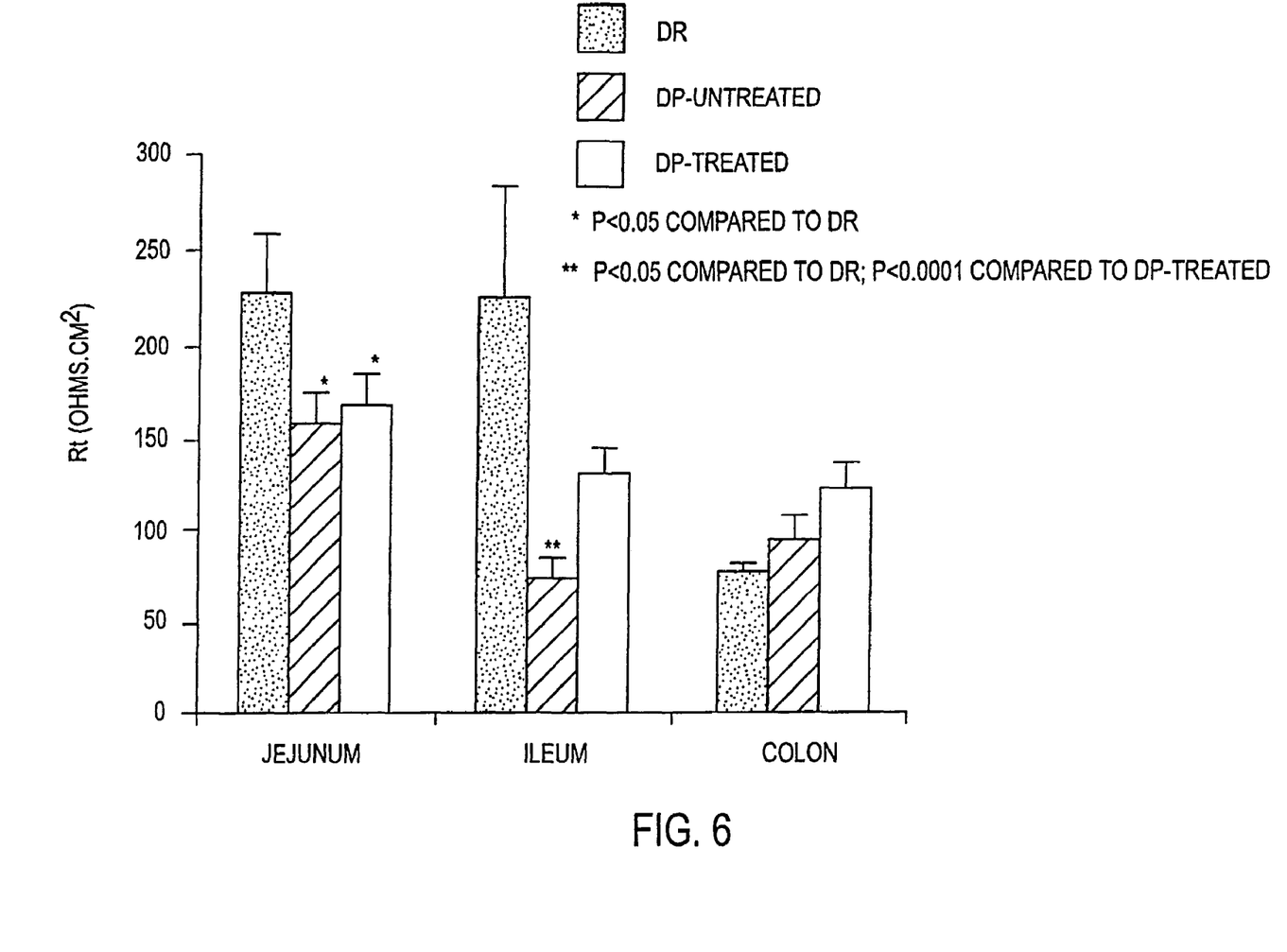
FIG. 6 shows ex vivo intestinal permeability in diabetic resistant (DR) rats, untreated diabetic-prone rats (DP-untreated; second bar) determined in Ussing chambers, diabetic-prone rats treated with the peptide antagonist of zonulin (DP-treated; third bar). * equals $p<0.05$; ** equals $p<0.05$, and $p<0.0001$ compared to DP-treated.

As demonstrated in the ex vivo Ussing chamber permeability studies, and shown in FIG. 6, all of the rats that progressed to diabetes had an increase in their intestinal permeability. Diabetic resistant (DR) rats had no appreciable alterations in paracellular permeability (first bar). Untreated diabetic-prone rats (DP-untreated; second bar) had a significant increase in paracellular permeability of the jejunum and ileum. More importantly, diabetic-prone rats treated with the peptide antagonist of zonulin (DP-treated; third bar) had a significant increase in paracellular permeability of the small intestine restricted to the jejunum. However, as shown in FIG. 6, pre-treatment with the zonulin peptide antagonist prevented these changes in the distal ileum. Consequently, alterations in paracellular permeability associated with the pathogenesis are restricted to the ileum. Also, as shown in FIG. 6, there are no significant changes in permeability of the colon, which coincides, with the regional distribution of the zonulin receptor distribution.

Figure 7:
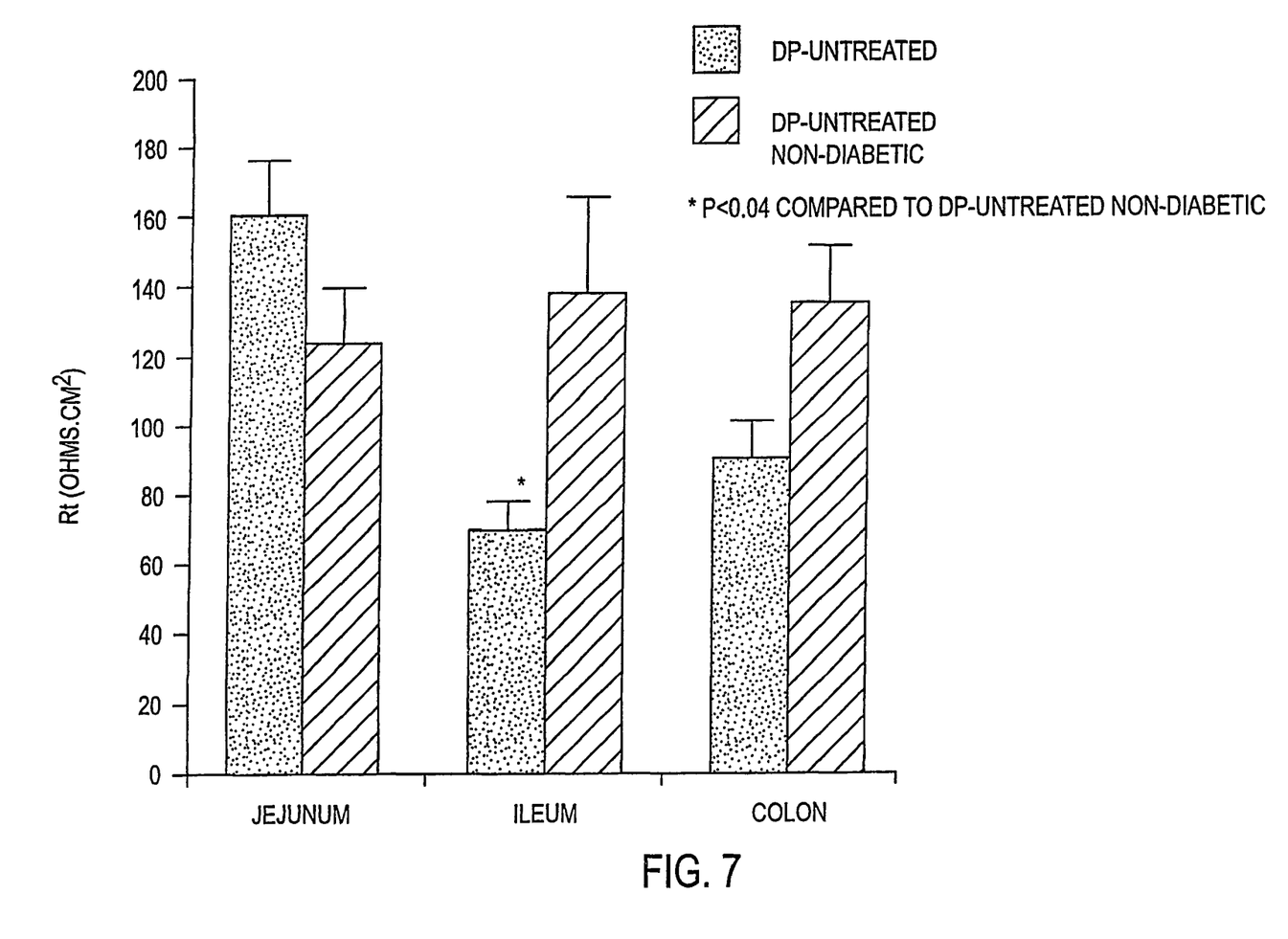
FIG. 7 shows ex vivo intestinal permeability in the small intestines of untreated diabetes-prone rats that either developed or did not develop diabetes. * equals $p<0.04$.

These results were further validated by a comparison of ex vivo intestinal permeability in the small intestines of untreated diabetes-prone rats that either developed (DP-D) or did not developed (DP-N) diabetes (FIG. 7). While no significant changes in jejunal Rt were observed between DP-D and DP-N rats, a significant lower Rt of the ileal mucosa of DP-D rats was observed as compared to DP-N rats (FIG. 7).

Thus, the following conclusions can be made: (1) the peptide antagonist was able to effectively block the permeability changes required for the development of diabetes; and (2) in those rats treated with the peptide antagonist, the levels of intraluminal zonulin are 3-fold higher than the treated rats that did not develop diabetes. In this population of treated rats that developed diabetes, the amount of peptide antagonist may not have been enough to block a sufficient number of ZOT/zonulin receptors necessary to prevent diabetes.

60% of the treated rats did not develop diabetes. In this population of rats, the peptide antagonist of zonulin effectively prevented the increase in intestinal permeability necessary for the onset of diabetes. As shown in FIG. 5, the treated rats had levels of intraluminal zonulin comparable with the untreated controls, but due to the presence of the peptide antagonist of zonulin, the overall permeability the small intestine was not altered enough to initiate the pathophysiologic changes necessary for the progression to diabetes. Interestingly, as shown in FIG. 5, the one control animal that did not develop diabetes had negligible levels of zonulin, further supporting the role of zonulin in the pathogenesis of diabetes.

Accordingly, an early event in the pathogenesis of diabetes in BB/Wor rats involves changes in zonulin-mediated intestinal paracellular permeability. Furthermore, inhibition of the zonulin signaling system with the use of peptide antagonists of zonulin prevents, or at least delays, the onset of diabetes.

While the invention has been described in detail, and with reference to specific embodiments thereof, it will be apparent to one of ordinary skill in the art that various changes and modifications can be made therein without departing from the spirit and scope thereof.

What is claimed:

1. A method for delaying progression of diabetes, comprising:
    administering to a diabetic patient, a pharmaceutically effective amount of a peptide antagonist of zonulin, wherein the peptide antagonist binds to zonula occludens toxin receptor but does not physiologically modulate the opening of mammalian intestinal tight junctions.

2. The method of claim 1, wherein the peptide antagonist comprises an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, and SEQ ID NO: 24.

3. The method of claim 1, wherein the peptide antagonist is from 8-110 amino acids in size.

4. The method of claim 1, wherein the peptide antagonist is from 8-40 amino acids in size.

5. The method of claim 1, wherein the peptide antagonist comprises amino acid sequence SEQ ID NO: 15.

6. The method of claim 1, wherein the peptide antagonist consists of amino acid sequence SEQ ID NO: 15.

7. The method of claim 1, wherein the peptide antagonist is administered as an oral dosage composition for intestinal delivery.

8. The method of claim 1, wherein the peptide antagonist consists of an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, and SEQ ID NO: 24.

9. The method of claim 1, wherein the patient has type I diabetes.

10. A method for delaying progression of diabetes, comprising:
    administering to the small intestine of a diabetic patient, a pharmaceutically effective amount of a peptide consisting essentially of the amino acid sequence of SEQ ID NO: 15.

11. The method of claim 10, wherein the patient has type 1 diabetes.

12. The method of claim 10, wherein the peptide is administered in a gastoresistant tablet or capsule.

* * * * *